United States Patent
Kurihara et al.

(10) Patent No.: US 10,392,325 B2
(45) Date of Patent: Aug. 27, 2019

(54) METHOD FOR PRODUCING FLUORINATED ALKANE, METHOD FOR SEPARATING AND RECOVERING AMIDINE BASE, AND METHOD FOR USING RECOVERED AMIDINE BASE

(71) Applicants: Kanto Denka Kogyo Co., Ltd., Chiyoda-ku, Tokyo (JP); ZEON CORPORATION, Chiyoda-ku, Tokyo (JP)

(72) Inventors: Kazuki Kurihara, Kurashiki (JP); Tatsuya Sugimoto, Tokyo (JP)

(73) Assignees: Kanto Denka Kogyo Co., Ltd., Chiyoda-ku, Tokyo (JP); ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 15/561,456

(22) PCT Filed: Mar. 29, 2016

(86) PCT No.: PCT/JP2016/060119
§ 371 (c)(1),
(2) Date: Sep. 25, 2017

(87) PCT Pub. No.: WO2016/158947
PCT Pub. Date: Oct. 6, 2016

(65) Prior Publication Data
US 2018/0118642 A1    May 3, 2018

(30) Foreign Application Priority Data

Mar. 31, 2015  (JP) .................. 2015-072219
Mar. 31, 2015  (JP) .................. 2015-072220

(51) Int. Cl.

| | | |
|---|---|---|
| *C07D 471/04* | (2006.01) | |
| *C07C 17/16* | (2006.01) | |
| *C07C 19/08* | (2006.01) | |
| *B01D 1/22* | (2006.01) | |
| *B01D 3/10* | (2006.01) | |
| *B01D 3/36* | (2006.01) | |

(52) U.S. Cl.
CPC .............. *C07C 17/16* (2013.01); *B01D 1/222* (2013.01); *B01D 3/10* (2013.01); *B01D 3/36* (2013.01); *C07C 19/08* (2013.01); *C07D 471/04* (2013.01)

(58) Field of Classification Search
CPC .................................................. C07D 471/04
See application file for complete search history.

(56) References Cited

U.S. PATENT DOCUMENTS 2,550,953  A    5/1951  Barrick
5,540,818  A    7/1996  Fujii et al.
5,760,255  A    6/1998  Vorbrueggen et al.
5,780,672  A    7/1998  Pasenok et al.
6,063,278  A    5/2000  Koo et al.

FOREIGN PATENT DOCUMENTS

| | | |
|---|---|---|
| JP | S5946251 A | 3/1984 |
| JP | H0226553 A | 1/1990 |
| JP | H06263715 A | 9/1994 |
| JP | H0948741 A | 2/1997 |
| JP | H09507503 A | 7/1997 |
| JP | 2001164033 A | 6/2001 |
| JP | 2002520302 A | 7/2002 |
| JP | 2002530356 A | 9/2002 |
| JP | 2009292749 A | 12/2009 |
| JP | 2011012164 A | 1/2011 |
| JP | 2011521781 A | 7/2011 |
| WO | 9613474 A1 | 5/1996 |
| WO | 0002840 A1 | 1/2000 |
| WO | 0031003 A1 | 6/2000 |
| WO | 2009145372 A1 | 12/2009 |

OTHER PUBLICATIONS

B.Bennua-Skalmowski et al., "A Facile Conversion of Primary or Secondary Alcohols with n-Perfluorobutane-sulfonyl Fluoride/1,8-Diazabicyclo[5.4.0]undec-7-ene into their Corresponding Fluorides", Tetrahedron Letters, Apr. 10, 1995, pp. 2611-2614, vol. 36, No. 15.
Handbook of Chemistry, 3rd revised ed., Pure Chemistry II, edited by the Chemical Society of Japan, Jun. 25, 1984, pp. 144-145, Maruzen Co., Ltd.
Helmut Vorbrüggen, "The Conversion of Primary or Secondary Alcohols with Nonaflyl Fluoride into Their Corresponding Inverted Fluorides", Synthesis, 2008, pp. 1165-1174, No. 8.
Jingjun Yin et al., "Direct and Convenient Conversion of Alcohols to Fluorides", Organic Letters, Mar. 31, 2004, pp. 1465-1468, vol. 6, No. 9.
Jun. 28, 2016, International Search Report issued in the International Patent Application No. PCT/JP2016/060119.
Matthew K. Nielsen et al., "PyFluor: A Low-Cost, Stable, and Selective Deoxyfluorination Reagent", Journal of the American Chemical Society, 2015, pp. 9571-9574, vol. 137, No. 30, Supporting Information, S3-S4.
T. Gramstad et al., "Perfluoroalkyl Derivatives of Sulphur. Part IV. Perfluoroalkanesulphonic Acids.", Journal of Chemical Society, 1956, pp. 173-180.

(Continued)

*Primary Examiner* — Brain E McDowell
(74) *Attorney, Agent, or Firm* — Kenja IP Law PC

(57) ABSTRACT

The present invention provides: a method for producing a fluorinated alkane represented by the formula (2): $R^2$—F, wherein an alcohol having 3 to 5 carbon atoms is fluorinated by a fluorinating agent represented by the formula (1): $R^1SO_2F$ in the absence of a solvent, and in the presence of an amidine base. In the formula, $R^1$ represents a methyl group, an ethyl group or an aromatic group, $R^2$ represents an alkyl group having 3 to 5 carbon atoms, and n is 0 or 2.

8 Claims, No Drawings

(56) References Cited

OTHER PUBLICATIONS

The Fifth Series of Experimental Chemistry 16, edited by the Chemical Society of Japan, Mar. 31, 2005, p. 228, particularly, experimental example 2.40 , Maruzen Co., Ltd.
Thomas A. Bianchi et al., "Phase Transfer Catalysis. Preparation of Aliphatic and Aromatic Sulfonyl Fluorides", The Journal of Organic Chemistry, 1977, pp. 2031-2032, vol. 42, No. 11.
Tomoya Kitazume et al., "Fluorination of Activated Halogens With KF in Polyethylene Glycol-Acetonitrile System", Chemistry Letters, 1978, pp. 283-284, published by the Chemical Society of Japan.

METHOD FOR PRODUCING FLUORINATED ALKANE, METHOD FOR SEPARATING AND RECOVERING AMIDINE BASE, AND METHOD FOR USING RECOVERED AMIDINE BASE

TECHNICAL FIELD

The present invention relates to a method for producing a fluorinated alkane having 3 to 5 carbon atoms safely and simply, economically and with a high yield, a method for separating and recovering an amidine base from the sulfonate complex of an amidine base by-produced in the production process of the fluorinated alkane, and a method for using the recovered amidine base.

BACKGROUND ART

Fluorinated alkanes are used as gases for plasma reactions, fluorine-containing intermediates of medicines, and media such as cooling/heating media. In particular, highly-purified fluorinated alkanes are suitably used as plasma etching gases, gases for the chemical vapor deposition method (CVD) and the like in the field of the production of semiconductor devices using plasma reactions.

As a method for producing a fluorinated alkane, there has hitherto been known a method in which an alkylsulfonyl fluoride is allowed to react as a fluorinating agent with a corresponding alcohol.

For example, Non Patent Literature 1 describes an example of the fluorination of the hydroxyl group in a steroid precursor by using, in a toluene solvent, a perfluorobutanesulfonyl fluoride as a fluorinating agent and 1,8-diazabicyclo[5.4.0]undec-7-ene (DBU) as a base.

Non Patent Literature 2 describes a method for fluorinating primary to tertiary alcohols, in a tetrahydrofuran or methylene chloride solvent, by using a ternary system of perfluorobutanesulfonyl fluoride-a trialkylamine-hydrogen fluoride complex-a trialkylamine.

Non Patent Literature 3 describes an example of the fluorination of various alcohols by using nonafluorobutanesulfonyl fluoride as a fluorinating agent, and DBU as a base.

Patent Literature 1 describes a fluorination of a high molecular weight alcohol compound, in a solvent such as toluene or diethylene glycol dimethyl ether, by using a fluoroaliphatic sulfonyl fluoride as a fluorinating agent, and DBU as a base.

Patent Literature 2 also describes a fluorination of an aliphatic alcohol, an aromatic hydrocarbon compound and an enol compound, in an inert organic solvent such as toluene, by using nonafluorobutanesulfonyl fluoride as a fluorinating agent, and an amidine base as a base.

However, the fluorinating agent used in these documents, namely, the perfluoroalkanesulfonyl fluoride is expensive, and thus not appropriate to industrial use. The perfluoroalkanesulfonic acid derivatives produced in the case where these fluorinating agents are used also suffer from an apprehension of long-term toxicity and a safety problem.

These documents also describe only the examples using alcohols relatively high in boiling temperature and complicated in structure as raw material alcohols; thus, when alcohols having 3 to 5 carbon atoms are used as raw materials, the possibility of the production of fluorinated alkanes having 3 to 5 carbon atoms is not clear.

On the other hand, the following methods are known as methods for producing fluorinated alkanes having 3 to 5 carbon atoms.

Patent Literature 3 describes a production of 2-fluorobutane at a yield of 46%, by bringing N,N'-diethyl-3-oxo-methyltrifluoropropyl amine as a fluorinating agent into contact with 2-butanol.

However, the N,N'-diethyl-3-oxo-methyltrifluoropropyl amine used may deserve to be referred to as an extremely expensive fluorinating agent because of being produced from 4-chloro-3,4,4-trifluoro-2-butanone, industrially difficult to obtain, and two equivalents of diethylamine. In addition, the yield of the target product, 2-fluorobutane, of 46% is not satisfactory.

Patent Literature 4 describes a production of 2-fluorobutane at a yield of 68% from 2-butanol by using triethylammonium hexafluorocyclobutane as a fluorinating agent in the absence of a solvent.

However, the triethylammonium hexafluorocyclobutane used is a product produced by using hexafluorocyclobutene industrially extremely expensive and strongly toxic.

Patent Literature 5 describes a production of fluorinated sec-butyl by bringing sulfur hexafluoride into contact with a sec-butyl lithium cyclohexane-hexane solution.

However, the sec-butyl lithium cyclohexane-hexane solution used is high in ignitability to offer a problem with respect to handling. In addition, sulfur hexafluoride has an extremely long atmospheric lifetime, resulting in a problem of safety.

Moreover, Patent Literature 6 describes a production of 2-fluorobutane by hydrogenating 2-fluorobutadiene in the presence of a catalyst.

However, the method described in this document encounters a problem that 2-fluorobutadiene, the raw material, is difficult to obtain.

As described above, the methods described in these documents are not capable of being said as favorable industrial production methods of fluorinated alkanes.

In these documents, there are no descriptions on, e.g., the method for treating or the method for recovering the sulfonate complex of the amidine base by-produced by using perfluorosulfonyl fluoride as a fluorinating agent and by using an amidine base as a base.

On the other hand, Patent Literature 7 describes a method of recovering, by adsorption with activated carbon, tetramethylpropane diamine contained in waste water as a method for recovering a water-soluble amine.

Patent Literature 8 also describes a method for recovering an amine as follows: the amine in waste water is adsorbed on a cation exchange resin, then desorbed from the cation exchange resin by using an alkaline solution as an eluent, and the eluate is concentrated to recover the amine.

However, these documents describe the recovering of the amine from waste water with an adsorbent, in consideration of the reduction of environmental effect and load, but do not describe the handling of the recovered amine.

The amidine base such as DBU is a base extremely expensive for industrial use, and the amidine base is desired to be recovered and reused as much as possible from the viewpoint of the cost reduction.

CITATION LIST

Patent Literature

Patent Literature 1: National Publication of International Patent Application No. 2002-530356
Patent Literature 2: National Publication of International Patent Application No. 1997-507503

Patent Literature 3: Japanese Patent Laid-Open No. 59-46251
Patent Literature 4: Japanese Patent Laid-Open No. 09-48741
Patent Literature 5: Japanese Patent Laid-Open No. 2009-292749
Patent Literature 6: U.S. Pat. No. 2,550,953
Patent Literature 7: Japanese Patent Laid-Open No. 02-26553
Patent Literature 8: Japanese Patent Laid-Open No. 2011-521781

Non Patent Literature

Non Patent Literature 1: Tetrahedron Letters, Vol. 36, 2614 (1995)
Non Patent Literature 2: Organic Letters, Vol. 6, 1465 (2004)
Non Patent Literature 3: Synthesis, No. 8, 1165 (2008)

SUMMARY OF INVENTION

Technical Problem

The present invention was conceived in view of the above situation. First, an object of the present invention is to provide a method for industrially advantageously producing a fluorinated alkane having 3 to 5 carbon atoms. Secondly, another object of the present invention is to provide a method for industrially advantageously separating and recovering an amidine base from a sulfonate complex of the amidine base produced in the reaction of fluorinating an alcohol by using a sulfonyl fluoride as a fluorinating agent in the presence of the amidine base, and further a method for reusing the recovered amidine base.

Solution to Problem

The present inventors conducted extensive studies in order to solve the above problem, and as a result, found that by allowing a fluorinating agent represented by the formula (1): $R^1SO_2F$ ($R^1$ represents a methyl group, an ethyl group or an aromatic group) to act on an alcohol having 3 to 5 carbon atoms in the absence of a solvent and in the presence of an amidine base and the like, a fluorinated alkane (hereinafter, sometimes referred to as "a fluorinated alkane having 3 to 5 carbon atoms") represented by the formula (2): $R^2$—F ($R^2$ represents an alkyl group having 3 to 5 carbon atoms) can be obtained safely and simply, economically, and with a high yield.

The present inventors found that the amidine base can be simply and efficiently separated and recovered by performing the following three steps (I) to (III): a sulfonic acid alkali metal salt is precipitated by adding an alkaline aqueous solution to a solution obtained by dissolving the sulfonate complex of the by-produced amidine base in an aromatic hydrocarbon (step (I)); the sulfonic acid alkali metal salt is dissolved by adding water to the resulting mixture, and the aqueous layer having the sulfonic acid alkali metal salt dissolved is removed (step (II)); and the aromatic hydrocarbon is distilled off from the obtained aromatic hydrocarbon solution of the amidine base (step (III)); and also found that a fluorinated alkane can be produced by using the recovered amidine base. These findings have led to the completion of the present invention.

Thus, according to the present invention, the following methods [1] to [6] for producing a fluorinated alkane; the following methods [7] to [12] for separating and recovering the amidine base; and the following method [13] for using the recovered amidine base are provided.

[1] A method for producing a fluorinated alkane represented by the formula (2): $R^2$—F ($R^2$ represents an alkyl group having 3 to 5 carbon atoms), wherein an alcohol having 3 to 5 carbon atoms is fluorinated by a fluorinating agent represented by the formula (1): $R^1SO_2F$ ($R^1$ represents a methyl group, an ethyl group or an aromatic group) in the absence of a solvent, and in the presence of a base selected from the group consisting of an amidine base and a phosphazene base.

[2] The method for producing a fluorinated alkane according to [1], wherein the reaction is performed by adding the fluorinating agent to the mixture of the alcohol having 3 to 5 carbon atoms and the base at 60° C. to 150° C.

[3] The method for producing a fluorinated alkane according to [1] or [2], wherein the fluorinating agent is methanesulfonyl fluoride.

[4] The method for producing a fluorinated alkane according to any one of [1] to [3], wherein the base is the amidine base represented by the following formula (4):

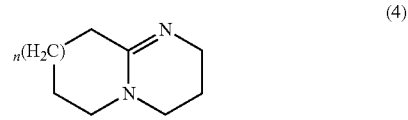

(in the formula, n is 0 or 2).

[5] The method for producing a fluorinated alkane according to any one of [1] to [4], wherein the base is 1,8-diazabicyclo[5.4.0]undec-7-ene.

[6] The method for producing a fluorinated alkane according to any one of [1] to [5], wherein the fluorinated alkane is 2-fluorobutane.

[7] A method for separating and recovering an amidine base from an amidine base-sulfonate complex represented by the following formula (5):

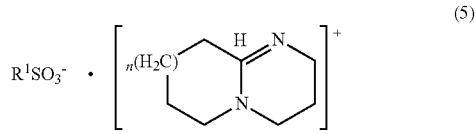

(in the formula, $R^1$ represents a methyl group, an ethyl group or an aromatic group, and n is 0 or 2), the method comprising:

a step (I) of adding an alkaline aqueous solution to a solution obtained by dissolving an amidine base-sulfonate complex in an aromatic hydrocarbon, to precipitate a sulfonic acid alkali metal salt;

a step (II) of adding water to the solution having the sulfonic acid alkali metal salt precipitated obtained in the step (I) to dissolve the sulfonic acid alkali metal salt, separating the aqueous layer having the sulfonic acid alkali metal salt dissolved and the layer of the aromatic hydrocarbon solution containing the amidine base from each other, and removing the aqueous layer having the sulfonic acid alkali metal salt dissolved; and a step (III) of distilling off the aromatic hydrocarbon from the aromatic hydrocarbon solution containing the amidine base obtained in the step (II).

[8] The method for separating and recovering an amidine base according to [7], wherein the amidine base-sulfonate complex is obtained from the reaction mixture obtained by performing a reaction of fluorinating an alcohol having 3 to 5 carbon atoms, by using a fluorinating agent represented by the formula (1): $R^1SO_2F$ ($R^1$ represents a methyl group, an ethyl group, or an aromatic group) in the absence of a solvent and in the presence of an amidine base represented by the following formula (4):

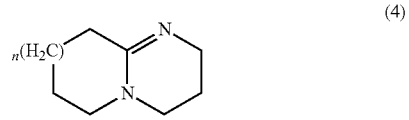

(4)

(in the formula, n is 0 or 2).

[9] The method for separating and recovering an amidine base according to [7] or [8], wherein the amidine base-sulfonate complex is 1,8-diazabicyclo[5.4.0]undec-7-ene-methanesulfonate complex.

[10] The method for separating and recovering an amidine base according to any one of [7] to [9], including, after the step (II) and before the step (III), a step (IV) of removing moisture contained in the aromatic hydrocarbon solution containing the amidine base obtained in the step (II).

[11] The method for separating and recovering an amidine base according to [10], wherein the step (IV) is a step of removing the moisture contained in the aromatic hydrocarbon solution containing the amidine base obtained in the step (II) by using a Dean-Stark water separator.

[12] The method for separating and recovering an amidine base according to any one of [7] to [11], wherein the amidine base is 1,8-diazabicyclo[5.4.0]undec-7-ene.

[13] A method for using a recovered amidine base, wherein the amidine base separated and recovered by the method according to any one of [7] to [12] is used as the base in the reaction of producing a fluorinated alkane represented by the formula (2): $R^2$—F ($R^2$ represents an alkyl group having 3 to 5 carbon atoms) by fluorinating an alcohol having 3 to 5 carbon atoms in the presence of a base by a fluorinating agent represented by the formula (1): $R^1SO_2F$ ($R^1$ represents a methyl group, an ethyl group or an aromatic group).

Advantageous Effects of Invention

According to the present invention, a fluorinated alkane having 3 to 5 carbon atoms can be produced which is suitable as a plasma etching gas, a gas for CVD and the like, by using a raw material and a fluorinating agent industrially available at low prices, safely and simply, economically and at a high yield.

According to the present invention, the amidine base can be separated and recovered simply and efficiently from the amidine base-sulfonate complex produced in the reaction fluorinating an alcohol by a sulfonyl fluoride in the presence of an amidine base. Accordingly, while the amount of the amidine base-sulfonate complex which is a very viscous oily substance and difficult to handle and discard is being reduced and the handleability is being improved, the environmental load can be reduced.

According to the present invention, by recovering and using the very expensive amidine base, the cost reduction can be achieved.

DESCRIPTION OF EMBODIMENTS

1) A method for producing a fluorinated alkane, 2) a method for separating and recovering an amidine base, and 3) a method for using the recovered amidine base according to the exemplary embodiments of the present invention are described in detail below.

1) Method for Producing a Fluorinated Alkane

A first aspect of the present invention is a method for producing a fluorinated alkane represented by the formula (2): $R^2$—F, wherein an alcohol having 3 to 5 carbon atoms is fluorinated by a fluorinating agent represented by the formula (1): $R'SO_2F$ in the absence of a solvent, and in the presence of a base selected from the group consisting of an amidine base and a phosphazene base.

(Raw Material Alcohol)

The production method of the present invention uses as a raw material an alcohol having 3 to 5 carbon atoms. An alcohol compound to yield the targeted fluorinated alkane may be selected and used.

Examples of the alcohol having 3 to 5 carbon atoms include: alcohols having 3 carbon atoms such as 1-propanol and 2-propanol; alcohols having 4 carbon atoms such as 1-butanol, 2-butanol, isobutanol, t-butanol, and cyclobutanol; alcohols having 5 carbon atoms such as 1-pentanol, 2-pentanol, 3-pentanol, 3-methyl-1-butanol, 3-methyl-2-butanol, 2-methyl-1-butanol, 2-methyl-2-butanol, 2,2-dimethyl-1-propanol, and cyclopentanol.

Among these, in the present invention, from the viewpoint of the handling easiness, usefulness and the like of the produced fluorinated alkane, alcohols having 4 or 5 carbon atoms are preferable; more preferable are 2-pentanol, 3-pentanol, cyclopentanol, 1-butanol, 2-butanol, isobutanol, and t-butanol.

(Fluorinating Agent)

In the present invention, as the fluorinating agent, a compound represented by the formula (1): $R^1SO_2F$ is used.

In the formula (1), $R^1$ represents a methyl group, an ethyl group or an aromatic group. Examples of the aromatic group include a phenyl group, a 1-naphthyl group and a 2-naphthyl group. These aromatic groups may each have a substituent such as a methyl group or an ethyl group.

Specific examples of the compound represented by the formula (1) include: aliphatic sulfonyl fluorides such as methanesulfonyl fluoride and ethanesulfonyl fluoride; and aromatic sulfonyl fluorides such as benzenesulfonyl fluoride and p-toluenesulfonyl fluoride. Among these, from the viewpoint of yielding target products economically with high yields and the handling easiness, methanesulfonyl fluoride and ethanesulfonyl fluoride are preferable, and methanesulfonyl fluoride is more preferable.

The compound represented by the formula (1) can be produced by using a heretofore known method.

For example, an aliphatic sulfonyl fluoride can be produced, for example, by a method in which a sulfonyl chloride is brought into contact with an alkali metal fluoride such as sodium fluoride or potassium fluoride in a water solvent (Japanese Patent Laid-Open No. 06-263715), and a method in which a sulfonyl chloride is brought into contact with potassium hydrogen difluoride in a water solvent (Journal of Chemical Society, 173 (1956)).

In addition, an aromatic sulfonyl fluoride can be produced, for example, by a method in which an aromatic sulfonyl chloride is used as a starting material, and a fluorination is performed by using potassium fluoride as a fluorinating agent in the presence of polyethylene glycol or 18-crown-6-ether as a phase-transfer catalyst (Chemistry Letters, 283 (1978), Journal of Organic Chemistry, Vol. 42, 2031 (1977)).

In the present invention, such inexpensive and easily available fluorinating agents as described above are used.

The amount of a fluorinating agent used is preferably ⅓ to 1 equivalent and more preferably ½ to ¾ equivalent in relation to the raw material alcohol. When the fluorinating agent is used excessively in relation to the raw material alcohol, the fluorinating agent is not efficiently consumed in an unpreferable manner. On the other hand, when the amount of the fluorinating agent used is too small, a wastefulness of the raw material is caused.

(Base)

The base used in the present invention is a base selected from the group consisting of an amidine base and a phosphazene base.

The amidine base is a basic organic compound having a skeleton of —N—C=N—. The amidine base may be an open chain compound, or an alicyclic ring, a bicyclic ring or a tricyclic ring having 4 to 8 ring members, preferably 5 or 6 ring members. The amidine base used in the present invention is a compound having preferably 4 to 20 carbon atoms, more preferably 4 to 14 carbon atoms, and still more preferably 4 to 10 carbon atoms.

Specific examples of the amidine base include, without being limited to: 7-methyl-1,5,7-triazabicyclo[4.4.0]dec-5-ene (MTBD), diazabicyclo[4.3.0]non-5-ene (DBN), and 1,8-diazabicyclo[5.4.0]-undec-7-ene (DBU).

The phosphazene base is a basic organic compound having a skeleton of (—N—)$_3$P=N— in the molecule thereof. Examples of the phosphazene base include, without being limited to: t-butyliminotris(dimethylaminophosphorane) (abbreviation: P$_1$-t-Bu), 1-t-butyl-4,4,4-tris(dimethylamino)-2,2-bis[tris(dimethylamino)phosphoranylideneamino]-2Λ$^5$,4Λ$^5$-catenadi(phosphazene) (abbreviation: P$_4$-t-Bu).

Among these, from the viewpoint of easy availability, the amidine base is preferable, and the amidine base having the skeleton represented by the following formula (4) is more preferable.

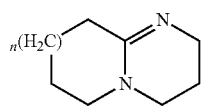

(4)

(in the formula, n is an integer of 0 or 2).

Specific examples of the compound having the above-described skeleton include 1,8-diazabicyclo[5.4.0]undec-7-ene (DBU) and 1,5-diazabicyclo[4.3.0]non-5-ene (DBN), and DBU is particularly preferable.

The amount of the base used is preferably 1 to 2 equivalents and more preferably 1 to 1.5 equivalents in relation to the fluorinating agent. When the amount of the base used is too small, unpreferably the yield is degraded. On the other hand, when the amount of the base used is too large, the viscosity of the reaction solution is large, and the treatment after the completion of the reaction is troublesome.

(Reaction)

The reaction is performed under a solvent-free condition.

The mixing order of the raw material alcohol, the base, and the fluorinating agent is not particularly limited; however, from the viewpoint of obtaining the target product in a good yield, preferably the raw material alcohol and the base are mixed with each other, and the fluorinating agent is added (added dropwise) to the resulting mixture. The fluorinating agent may be added all at once, or may be added little by little.

The reaction temperature is usually 50° C. to 150° C., preferably 60° C. to 150° C., and more preferably 60° C. to 100° C.

In the present invention, preferably, the mixture of the raw material alcohol and the base is preliminarily increased in the temperature falling within the above-described range, then fluorinating agent is added dropwise, and after the completion of the dropwise addition, the reaction is further allowed to proceed within the above-described temperature range.

When the reaction initiation temperature and the subsequent reaction temperature are lower than the above-described temperature range, there is a risk of causing a trouble such as a decrease of the raw material conversion rate, or an extremely prolonged reaction time. On the other hand, when the reaction initiation temperature and the reaction temperature are higher than the above-described temperature range, depending on the type of the raw material alcohol used, the alcohol is distilled along with the product, namely the fluorinated alkane, and the decrease of the yield tends to be caused.

The reaction time depends on the type of the raw material alcohol and the type of the base, and is usually 1 to 48 hours and preferably 3 to 20 hours. When the reaction time is too short, the conversion rate of the raw material alcohol is decreased, and the yield decrease of the target product is caused. On the other hand, when the reaction time is too long, the energy cost waste is unpreferably caused.

After the completion of the reaction, when the product (target product) has a boiling temperature lower than the reaction temperature, the product can be collected in a receiver outside the reaction system, connected to the reaction vessel and cooled with a cooling medium such as dry ice-ethanol, and recovered.

When the product (target product) has a boiling temperature higher than the reaction temperature, the product can be recovered, after the termination of the reaction under a reduced pressure, in a receiver cooled with a cooling medium or the like. In this case, the recovered unreacted alcohol can be reused as a raw material.

The fluorinated alkane collected in the receiver is subjected, if necessary, to a purification such as distillation purification to be able to be further increased in purity.

(Fluorinated Alkane)

As described above, the fluorinated alkane represented by the formula (2) can be produced.

In the formula (2), R$^2$ represents an alkyl group having 3 to 5 carbon atoms. Examples of the alkyl group having 3 to 5 carbon atoms include: alkyl groups having 3 carbon atoms such as a n-propyl group, an isopropyl group and a cyclopropyl group; alkyl groups having 4 carbon atoms such as a n-butyl group, a sec-butyl group, an isobutyl group, a t-butyl group and a cyclobutyl group; and alkyl groups having 5 carbon atoms such as a n-pentyl group, a 2-pentyl group, a 3-pentyl group, a 3-methyl-1-butyl group, a 3-methyl-2-butyl group, a 2-methyl-1-butyl group, a 2-methyl-2-butyl group, a 2,2-dimethyl-1-propyl group, and a cyclopentyl group.

Specific examples of the fluorinated alkane represented by the formula (2) include: fluorinated alkanes having 3 carbon atoms such as 1-fluoropropane and 2-fluoropropane; fluorinated alkanes having 4 carbon atoms such as 1-fluorobutane, 2-fluorobutane, 1-fluoro-2-methylpropane, t-butyl fluoride and fluorocyclobutane; and fluorinated alkanes having 5 carbon atoms such as 1-fluoropentane, 2-fluoropentane, 3-fluoropentane, 3-methyl-1-fluorobutane, 3-methyl-2-fluorobutane, 2-methyl-1-fluorobutane, 2-methyl-2-fluorobutane, 2,2-dimethyl-1-fluoropropane and fluorocyclopentane.

Among these, 2-fluorobutane is preferable from the viewpoint of being capable of more easily achieving the advantageous effects of the present invention. 2-Fluorobutane can be produced by using 2-butanol as a raw material alcohol.

In this way, according to the production method of the present invention, a fluorinated alkane having 3 to 5 carbon atoms can be produced by using a raw material and a fluorinating agent industrially available at low prices, without using any solvent, safely, simply, at a low cost and with a high yield.

2) Method for Separating and Recovering Amidine Base

A second aspect of the present invention is a method for separating and recovering the amidine base represented by the following formula (4) from the amidine base-sulfonate complex (hereinafter, simply referred to as "the amidine base-sulfonate complex") represented by the following formula (5):

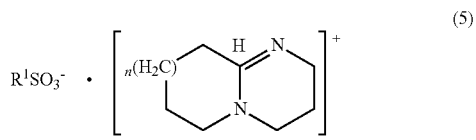

(5)

(in the formula, $R^1$ and n represent the same meanings as described above),

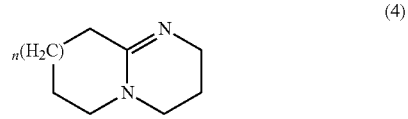

(4)

(in the formula, n represents the same meaning as described above); and the method for separating and recovering an amidine base includes the following steps (I) to (III):

step (I): a step of adding an alkaline aqueous solution to a solution obtained by dissolving an amidine base-sulfonate complex in an aromatic hydrocarbon, to precipitate a sulfonic acid alkali metal salt;

step (II): a step of adding water to the solution having the sulfonic acid alkali metal salt precipitated obtained in the step (I) to dissolve the sulfonic acid alkali metal salt, separating the aqueous layer having the sulfonic acid alkali metal salt dissolved and the layer of the aromatic hydrocarbon solution containing the amidine base from each other, and removing the aqueous layer having the sulfonic acid alkali metal salt dissolved; and step (III): a step of distilling off the aromatic hydrocarbon from the aromatic hydrocarbon solution containing the amidine base obtained in the step (II).

The amidine base-sulfonate complex used in the present invention is a salt constituted with the amidine base represented by the formula (4) and the sulfonic acid represented by the formula: $R^1$—$SO_3H$ ($R^1$ represents the same meaning as described above). Specific examples of the amidine base-sulfonate complex include: aliphatic sulfonate complexes such as DBU-methanesulfonate complex, DBU-ethanesulfonate complex, 1,5-diazabicyclo[4.3.0]non-5-ene (DBN)-methanesulfonate complex, and DBN-ethanesulfonate complex; and aromatic sulfonate complexes such as DBU-benzene sulfonate complex, DBU-p-toluenesulfonate complex, DBN-benzenesulfonate complex, and DBN-p-toluenesulfonate complex.

Among these, from the viewpoint of more remarkably achieving the advantageous effects of the present invention, the aliphatic sulfonate complexes are preferable, and DBU-methanesulfonate complex is particularly preferable.

(Step (I))

In the present invention, the step (I) is a step of adding an alkaline aqueous solution to a solution obtained by dissolving an amidine base-sulfonate complex in an aromatic hydrocarbon, to precipitate a sulfonic acid alkali metal salt.

As the aromatic hydrocarbon used in the present invention, an aromatic hydrocarbon dissolving the amidine base-sulfonate complex and forming an azeotropic mixture composition with water is preferable. Specific examples of such an aromatic hydrocarbon include: alkyl-substituted benzenes such as benzene, toluene, xylene, and ethyl benzene; and halogen-substituted benzenes such as fluorobenzene, chlorobenzene, and dichlorobenzene. Among these, the alkyl-substituted benzenes are preferable, and toluene being able to be distilled off at a relatively low temperature is more preferable.

The amount of the aromatic hydrocarbon used depends on the scale of the reaction or the like, but is usually 0.7 to 1 ml in relation to 1 g of the amidine base-sulfonate complex. When the amount of the aromatic hydrocarbon used is too small, there is a possibility that the extraction efficiency of the amidine base is degraded. On the other hand, when the amount of the aromatic hydrocarbon used is too large, the distillation off of the aromatic hydrocarbon in the subsequent step requires a considerable time to degrade the productivity.

The alkaline aqueous solution used in the present invention is not particularly limited as long as the alkaline aqueous solution forms a salt with the sulfonic acid constituting the amidine base-sulfonate complex, and thus precipitates the sulfonic acid salt, when the alkaline aqueous solution is added to an aromatic hydrocarbon solution of the amidine base-sulfonate complex.

Among such alkaline aqueous solutions, from the viewpoint of being excellent in the affinity with water, aqueous solutions of alkali metal hydroxides such as sodium hydroxide, potassium hydroxide, and cesium hydroxide are preferable; aqueous solutions of potassium hydroxide and cesium hydroxide are more preferable; and an aqueous solution of potassium hydroxide is particularly preferable which is inexpensive and leads to a large solubility in water of the produced sulfonic acid salt.

The alkali metal hydroxide itself usually presents as a pellet or a flaky solid; however, the alkali metal hydroxide is used as an aqueous solution from the viewpoint of easy industrial handling.

The concentration of the alkaline aqueous solution used is not particularly limited, but is preferably approximately 10 wt % to 50 wt %. When the concentration of the alkaline aqueous solution is too low, a large amount of the alkaline aqueous solution is required in order to neutralized the sulfonic acid in the amidine base-sulfonate complex and to liberate the amidine base, accordingly the volume of the waste water is increased, the extraction effect of the amidine base is decreased, and the recovery rate is degraded. On the other hand, when the concentration of the alkaline aqueous solution is too high, the evolution of heat is large at the time of neutralizing the sulfonic acid in the amidine base-sulfonate complex, and a danger is liable to be involved.

The amount of the alkali used in the alkaline aqueous solution is usually 0.9 to 1.5 equivalents in relation to the amidine base-sulfonate complex. When the amount of the alkali (the alkaline aqueous solution) used is too small, the neutralization reaction with the sulfonic acid is not completed, and the recovery rate of the amidine base is degraded. On the other hand, when the amount of the alkali (the alkaline aqueous solution) used is too large, the disposal of the waste solution is troublesome.

As the method for adding the alkaline aqueous solution to the aromatic hydrocarbon solution of the amidine base-sulfonate complex, a method in which while the aromatic hydrocarbon solution is being stirred, the alkaline aqueous solution is added dropwise within the solution temperature range from 0° C. to room temperature (25° C.±10° C., hereinafter the same shall apply) is preferable. When the addition temperature is too low, the aromatic hydrocarbon solution of the amidine base-sulfonate complex is in a viscous state, and the neutralization reaction between the sulfonic acid and the alkali does not proceed smoothly. On the other hand, when the addition temperature is too high, the neutralization reaction between the sulfonic acid and the alkali proceeds rapidly, and unpreferably a failure such bumping is liable to occur.

When the alkaline aqueous solution is added dropwise at a temperature of 0° C. to room temperature to the aromatic hydrocarbon solution of the amidine base-sulfonate complex while the aromatic hydrocarbon solution of the amidine base-sulfonate complex is being stirred, the neutralization reaction proceeds, the amidine base is liberated, and at the same time, the alkali metal salt of the sulfonic acid is precipitated.

(Step (II))

In the present invention, the step (II) is a step of adding water to the solution having the sulfonic acid alkali metal salt precipitated obtained in the step (I) to dissolve the sulfonic acid alkali metal salt, and removing the aqueous layer having the sulfonic acid alkali metal salt dissolved.

When water is added to the solution having the sulfonic acid alkali metal salt precipitated, the solution is separated into two layers, namely, an aqueous layer having the sulfonic acid alkali metal salt dissolved and the aromatic hydrocarbon layer (organic layer) dissolving the liberated amidine base.

The amount of water to be added may be an amount required for dissolving the sulfonic acid alkali metal salt. When the amount of water to be added is too small, an unresolved fraction of the sulfonic acid alkali metal salt remains, the two-layer separation with the organic layer having the liberated amidine base dissolved (extracted) is difficult. On the other hand, the amount of water to be added is too large, the extraction effect of the amidine base is small, and a failure such as the degraded recovery rate occurs.

By removing the lower layer, namely, the aqueous layer having the sulfonic acid alkali metal salt dissolved, the aromatic hydrocarbon solution containing the extracted amidine base can be obtained.

It is to be noted that the amidine base is water soluble, and accordingly, in order to increase the extraction efficiency of the amidine base, an extraction operation may be performed by further adding the aromatic hydrocarbon to the aqueous layer having the sulfonic acid alkali metal salt dissolved.

(Step (III))

The step (III) of the present invention is a step of distilling off the aromatic hydrocarbon from the aromatic hydrocarbon solution containing the amidine base obtained in the step (II).

Examples of the method for distilling off the aromatic hydrocarbon from the aromatic hydrocarbon solution containing the amidine base include, without being particularly limited to: a method using a concentration device such as a rotary evaporator under reduced pressure.

Thus, the amidine base can be recovered.

The amidine base recovered in this way sometimes includes a small amount of a tar component and small amounts of salts (for example, a sulfonic acid alkali metal salt), and accordingly, when a further higher purity amidine base is desired to be obtained, a purification step such as a reduced pressure distillation is preferably arranged.

(Step (IV))

When the recovered amidine base is reused or the like, the amidine base preferably contains no moisture. However, the aromatic hydrocarbon solution of the amidine base obtained in the step (II) contains moisture in many cases. Accordingly, after the step (II) and before the step (III), preferably arranged is a step (IV) of removing moisture from the aromatic hydrocarbon solution containing the amidine base obtained in the step (II).

Examples of the method for removing moisture from the aromatic hydrocarbon solution containing the amidine base include: a method in which a dehydrating agent such as a molecular sieve, anhydrous magnesium sulfate or anhydrous sodium sulfate is added to the aromatic hydrocarbon solution, the moisture is absorbed by the dehydrating agent, and then the dehydrating agent having absorbed the moisture is separated and removed; and a method for removing the moisture by using a Dean-Stark water separator; the latter method is preferable. According to the Dean-Stark water separator, by taking advantage of the property of the aromatic hydrocarbon to azeotropically boil with water, water and the aromatic hydrocarbon are azeotropically boiled by heating, and thus the moisture can be efficiently removed.

The azeotropic temperatures of aromatic hydrocarbons and water are, for example, as follows. Toluene:water=80.1:19.9 (weight ratio, hereinafter the same shall apply) (boiling temperature: 85° C.), o-xylene:water=50.1:49.9 (boiling temperature: 93.5° C.), m-xylene:water=60.0:40.0 (boiling temperature: 94.5° C.), ethylbenzene:water=67.0:33.0 (boiling temperature: 92° C.), chlorobenzene:water=71.6:28.4 (boiling temperature: 90.2° C.) (all at atmospheric pressure) (Handbook of Chemistry, 3rd revised ed., Pure Chemistry II, edited by the Chemical Society of Japan).

For example, in the case where toluene is used as the aromatic hydrocarbon, when the weight ratio between toluene and water is 80.1:19.9, the azeotropic temperature is 85° C. Accordingly, by using a Dean-Stark water separator, a toluene solution dissolving an amidine base is continuously heated at a temperature higher than 85° C., and thus water is removed by the azeotropy with toluene. When the distillation amount of water shows no variation, the heating is terminated, and then the step (III) may be performed.

3) Method for Using Recovered Amidine Base

A third aspect of the present invention is a method for using a recovered amidine base, wherein the amidine base separated and recovered by the method of the present invention is used as the base in the reaction of producing a fluorinated alkane represented by the formula (2): $R^2$—F by fluorinating an alcohol having 3 to 5 carbon atoms in the presence of a base by a fluorinating agent represented by the formula (1): $R^1SO_2F$.

Examples of the alcohol having 3 to 5 carbon atoms used in the present invention include: alcohols having 3 carbon atoms such as 1-propanol and 2-propanol; alcohols having 4 carbon atoms such as 1-butanol, 2-butanol, isobutanol, t-butanol and cyclobutanol; and alcohols having 5 carbon atoms such as 1-pentanol, 2-pentanol, 3-pentanol, 3-methyl-1-butanol, 3-methyl-2-butanol, 2-methyl-1-butanol, 2-methyl-2-butanol, 2,2-dimethyl-1-propanol and cyclopentanol.

Among these, in the present invention, from the viewpoint of the handling easiness, usefulness and the like of the produced fluorinated alkane, alcohols having 4 or 5 carbon atoms are preferable; more preferable are 2-pentanol, 3-pentanol, cyclopentanol, 1-butanol, 2-butanol, isobutanol, and t-butanol.

In the present invention, as the fluorinating agent, a compound represented by the formula (2): $R^1SO_2F$ ($R^1$ represents the same meaning as described above) is used.

Specific examples of the compound represented by the formula (2) include: aliphatic sulfonyl fluorides such as methanesulfonyl fluoride and ethanesulfonyl fluoride; and aromatic sulfonyl fluorides such as benzenesulfonyl fluoride and p-toluenesulfonyl fluoride. Among these, from the viewpoint of obtaining the target product economically in a good yield, methanesulfonyl fluoride and ethanesulfonyl fluoride are preferable, and methanesulfonyl fluoride is more preferable.

The compound represented by the formula (1) can be produced by using heretofore known methods.

For example, the aliphatic sulfonyl fluoride can be produced by a method in which a sulfonyl chloride is brought into contact in a water solvent with an alkali metal fluoride such as sodium fluoride or potassium fluoride (Japanese Patent Laid-Open No. 06-263715), or a method in which sulfonyl chloride is brought into contact in a water solvent with potassium hydrogen difluoride (Journal of Chemical Society, 173 (1956)).

The aromatic sulfonyl fluoride can be produced, for example, by a method in which an aromatic sulfonyl chloride is used as a starting material, and is fluorinated by using potassium fluoride as a fluorinating agent in the presence of polyethylene glycol or 18-crown-6-ether as a phase-transfer catalyst (Chemistry Letters, 283 (1978); Journal of Organic Chemistry, Vol. 42, 2031 (1977)).

The amount of the fluorinating agent used is preferably ⅓ to 1 equivalent and more preferably ½ to ¾ equivalent in relation to the raw material alcohol. When the fluorinating agent is used excessively in relation to the raw material alcohol, unpreferably the fluorinating agent is not consumed efficiently. On the other hand, when the amount of the fluorinating agent used is too small, a wastefulness of the raw material is caused.

The amount of the recovered amidine base used is preferably 1 to 2 equivalents and more preferably 1.1 to 1.5 equivalents in relation to the fluorinating agent. When the amount of the base used is too small, unpreferably the yield is degraded. On the other hand, when the amount of the base used is too large, the viscosity of the reaction solution is large, and the treatment after the completion of the reaction is troublesome.

The reaction is preferably performed under a solvent-free condition.

The mixing order of the raw material alcohol, the recovered amidine base, and the fluorinating agent is not particularly limited; however, from the viewpoint of obtaining the target product in a good yield, preferably the raw material alcohol and the base are mixed with each other, and the fluorinating agent is added (added dropwise) to the resulting mixture. The fluorinating agent may be added all at once, or may be added little by little.

The reaction temperature is usually 50° C. to 150° C., preferably 60° C. to 150° C., and more preferably 60° C. to 100° C.

In the present invention, preferably, the mixture of the raw material alcohol and the base is preliminarily increased in the temperature falling within the above-described range, then fluorinating agent is added dropwise, and after the completion of the dropwise addition, the reaction is further allowed to proceed within the above-described temperature range.

When the reaction initiation temperature and the subsequent reaction temperature are lower than the above-described temperature range, there is a risk of causing a trouble such as a decrease of the raw material conversion rate, or an extremely prolonged reaction time. On the other hand, when the reaction initiation temperature and the reaction temperature are higher than the above-described temperature range, depending on the type of the raw material alcohol used, the alcohol is distilled along with the product, namely the fluorinated alkane, and the decrease of the yield tends to be caused.

The reaction time depends on the type of the raw material alcohol and the type of the base, and is usually 1 to 48 hours and preferably 3 to 20 hours. When the reaction time is too short, the conversion rate of the raw material alcohol is decreased, and the yield decrease of the target product is caused. On the other hand, when the reaction time is too long, the energy cost waste is unpreferably caused.

After the completion of the reaction, when the product (target product) has a boiling temperature lower than the reaction temperature, the product can be collected in a receiver outside the reaction system, connected to the reaction vessel and cooled with a cooling medium such as dry ice-ethanol, and recovered.

When the product (target product) has a boiling temperature higher than the reaction temperature, the product can be recovered, after the termination of the reaction under a reduced pressure, in a receiver cooled with a cooling medium or the like. In this case, the recovered unreacted alcohol can be reused as a raw material.

The fluorinated alkane collected in the receiver is subjected, if necessary, to a purification such as distillation purification to be able to be further increased in purity.

As described above, the fluorinated alkane represented by the formula (2): $R^2$—F can be produced.

In the formula (2), $R^2$ represents an alkyl group having 3 to 5 carbon atoms. Examples of the alkyl group having 3 to 5 carbon atoms include: alkyl groups having 3 carbon atoms such as a n-propyl group, an isopropyl group and a cyclopropyl group; alkyl groups having 4 carbon atoms such as a n-butyl group, a sec-butyl group, an isobutyl group, a t-butyl group and a cyclobutyl group; and alkyl groups having 5 carbon atoms such as a n-pentyl group, a 2-pentyl group, a 3-pentyl group, a 3-methyl-1-butyl group, a 3-methyl-2-butyl group, a 2-methyl-1-butyl group, a 2-methyl-2-butyl group, a 2,2-dimethyl-1-propyl group, and a cyclopentyl group.

Specific examples of the fluorinated alkane represented by the formula (3) include: fluorinated alkanes having 3 carbon atoms such as 1-fluoropropane and 2-fluoropropane; fluorinated alkanes having 4 carbon atoms such as 1-fluorobutane, 2-fluorobutane, 1-fluoro-2-methylpropane, t-butyl fluoride and fluorocyclobutane; and fluorinated alkanes having 5 carbon atoms such as 1-fluoropentane, 2-fluoropentane, 3-fluoropentane, 3-methyl-1-fluorobutane, 3-methyl-2-fluorobutane, 2-methyl-1-fluorobutane, 2-methyl-2-fluorobutane, 2,2-dimethyl-1-fluoropropane and fluorocyclopentane.

In this way, according to the using method of the present invention, a fluorinated alkane having 3 to 5 carbon atoms can be produced by using the recovered amidine base simply, at a low cost and with a high yield.

EXAMPLES

Hereinafter, the present invention is further described in detail by way of examples, but the scope of the present invention is not limited by following examples. It is to be noted that the units "parts" and "%" respectively refer to "parts by weight" and "wt %" unless otherwise indicated.

The analysis conditions adopted in the following are as described below.

Gas Chromatography Analysis (GC Analysis)
Apparatus: HP-6890 (manufactured by Agilent Technologies, Inc.)
Column: Inert Cap-1, length: 60 m, inner diameter: 0.25 mm, film thickness: 1.5 μm (manufactured by GL Sciences Inc.)
Retention for 10 minutes at a column temperature of 40° C., successive temperature increase at 20° C./min, and subsequent retention for 10 minutes at 240° C.
Injection temperature: 200° C.
Carrier gas: nitrogen
Split ratio: 100/1
Detector: FID
Gas Chromatography Mass Analysis
GC section: HP-6890 (manufactured by Agilent Technologies, Inc.)
Column: Inert Cap-1, length: 60 m, inner diameter: 0.25 mm, film thickness: 1.5 μm (manufactured by GL Sciences Inc.)
Retention for 10 minutes at a column temperature of 40° C., successive temperature increase at 20° C./min, and subsequent retention for 10 minutes at 240° C.
MS section: 5973 NETWORK (manufactured by Agilent Technologies, Inc.)
Detector: EI type (acceleration voltage: 70 eV)
$^1$H-NMR Measurement and $^{19}$F-NMR Measurement
Apparatus: JNM-ECA-500 (JEOL Ltd.)

Production Example 1

Synthesis of methanesulfonyl fluoride

In a 500 ml volume glass reactor equipped with a stirring bar and a cooling condenser, 68 parts of potassium fluoride and 172 parts of water were placed, and potassium fluoride was dissolved by stirring the mixture. In the condenser, a cooling medium at 0° C. was circulated. Then, in the reactor, 115 parts of methanesulfonyl chloride was added, and after the completion of the addition, the mixture was stirred at a temperature of 50° C. for 7 hours. Subsequently, the reactor was cooled to room temperature, then 100 g of water was added to the reaction solution, and thus the salt (potassium chloride) precipitated during the reaction was dissolved. The contents in the reactor were transferred into a separating funnel, and allowed to stand still; then the organic layer, the lower layer, was separated. To the obtained organic layer, anhydrous magnesium sulfate was added, and the organic layer was dried. After magnesium sulfate was separated by filtration, the filtrate was distilled under reduced pressure (10 kPa, 55 to 56° C.), and thus 77 parts (yield: 79%) of methanesulfonyl fluoride, the target product, was obtained.

Production Example 2

Synthesis of ethanesulfonyl fluoride

In a 500 ml volume glass reactor equipped with a stirring bar and a cooling condenser, 68 parts of potassium fluoride and 173 parts of water were placed, and potassium fluoride was dissolved by stirring. In the condenser, a cooling medium at 0° C. was circulated. Then, in the reactor, 128 parts of ethanesulfonyl chloride was added, and after the completion of the addition, the mixture was stirred at a temperature of 50° C. for 8 hours. The reactor was cooled to room temperature, then 100 g of water was added to the reaction solution, and thus the salt (potassium chloride) precipitated in the reaction was dissolved. The contents in the reactor were transferred into a separating funnel, and allowed to stand still; then the organic layer, the lower layer, was separated. To the obtained organic layer, anhydrous magnesium sulfate was added, and the organic layer was dried. After magnesium sulfate was separated by filtration, the filtrate was distilled under reduced pressure (5 kPa, 54 to 55° C.), and thus 105 parts (yield: 94%) of ethanesulfonyl fluoride, the target product, was obtained.

Production Example 3

Synthesis of p-toluenesulfonyl fluoride

In a 300 ml volume glass reactor equipped with a stirring bar, 38 parts of p-toluenesulfonyl chloride, 68 parts of dried acetonitrile, and 1 part of 18-crown-6-ether were placed, and were stirred in a nitrogen atmosphere. In the resulting mixture, 24 parts of potassium fluoride was placed, and the mixture was stirred at room temperature for 15 hours. After the completion of the reaction, the reaction solution was introduced into water, and thus the total volume was made to be 500 ml. After being allowed to stand still, the organic layer as the lower layer was separated by decantation. The obtained organic layer was washed with pure water, and then allowed to stand at room temperature for 3 days. The precipitated white solid was collected, allowed to stand still in a desiccator, and dried under reduced pressure to yield 33 parts of white crystals (yield: 94%).

Example 1

In a 300 ml volume glass reactor equipped with a stirring bar, a dropping funnel, a thermometer and a collection receiver, 56.7 g of 2-butanol and 85.3 g of 1,8-diazabicyclo[5.4.0]undec-7-ene (DBU) were placed; then the contents were placed in a nitrogen atmosphere, and then the reactor was heated to 60° C. When the internal temperature became constant, 50 g of the methanesulfonyl fluoride obtained in Production Example 1 was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 27.6 g of 2-fluorobutane, the target product, was found to be obtained (yield with reference to methanesulfonyl fluoride: 71.2%).

The structure of the target product was identified on the basis of the $^1$H-NMR spectrum and the $^{19}$F-NMR spectrum.

$^1$H-NMR (CDCl$_3$, TMS, δ ppm): 0.88 (t, 3H), 1.17 (dq, 3H), 1.73 (m, 2H), 4.35 (m, 1H)

$^{19}$F-NMR (CDCl$_3$, CFCl$_3$, δ ppm): −173 (m, F)

Example 2

A reaction was performed in the same manner as in Example 1 except that the base was altered from 85.3 g of DBU in Example 1 to 69.7 g of 1,5-diazabicyclo[4.3.0]non-5-ene (DBN). The organic substance collected in the receiver was analyzed with gas chromatography, and 19.4 g of 2-fluorobutane, the target product, was found to be obtained (yield with reference to methanesulfonyl fluoride: 50%).

Example 3

A reaction was performed in the same manner as in Example 1 except that the raw material alcohol was altered from 56.7 g of 2-butanol in Example 1 to 45.9 g of 2-propanol. The organic substance collected in the receiver was analyzed with gas chromatography, and 19.7 g of 2-fluoropropane, the target product, was found to be obtained (yield with reference to methanesulfonyl fluoride: 60.7%).

The structure of the target product was identified on the basis of the $^1$H-NMR spectrum and the $^{19}$F-NMR spectrum.

$^1$H-NMR (CDCl$_3$, TMS, δ ppm): 1.32 (dd, 3H×2), 3.67 (m, H)

$^{19}$F-NMR (CDCl$_3$, CFCl$_3$, δ ppm): −165 ppm (m, F)

Example 4

A reaction was performed in the same manner as in Example 1 except that the raw material alcohol was altered from 56.7 g of 2-butanol in Example 1 to 67.4 g of 2-pentanol. The organic substance collected in the receiver was analyzed with gas chromatography, and 31.4 g of 2-fluoropentane, the target product, was found to be obtained (yield with reference to methanesulfonyl fluoride: 68.2%).

The structure of the target product was identified on the basis of the $^1$H-NMR spectrum and the $^{19}$F-NMR spectrum.

$^1$H-NMR (CDCl$_3$, TMS, δ ppm): 0.96 (t, 3H), 1.26 (d, 2H), 1.35 (m, 2H), 1.56 (m, 2H), 4.54-4.78 (m, 2H)

$^{19}$F-NMR (CDCl$_3$, CFCl$_3$, δ ppm): −173 ppm (m, F)

Example 5

In a 300 ml volume glass reactor equipped with a stirring bar, a dropping funnel, a thermometer and a collection receiver, 57 parts of 2-butanol and 85.3 g of DBU were placed; then the contents were placed in a nitrogen atmosphere, and then the reactor was heated to 60° C. When the temperature of the thermometer became constant, 57.2 g of the ethanesulfonyl fluoride produced in Production Example 2 was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 27.5 g of 2-fluorobutane, the target product, was found to be obtained (yield with reference to ethanesulfonyl fluoride: 70.9%).

Example 6

In a 300 ml volume glass reactor equipped with a stirring bar, a dropping funnel, a thermometer and a collection receiver, 56.7 g of 2-butanol and 88.8 g of p-toluenesulfonyl fluoride produced in Production Example 3 were placed; then the contents were placed in a nitrogen atmosphere, and then the reactor was heated to 60° C. When the temperature of the thermometer became constant, 85.3 g of DBU was added dropwise to the reactor from the dropping funnel over approximately 1.5 hours. After the completion of the dropwise addition, the reaction was continued at 60° C. for 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 21.3 g of 2-fluorobutane, the target product, was found to be obtained (yield with reference to p-toluenesulfonyl fluoride: 54.9%).

Example 7

In a 300 ml volume glass reactor equipped with a stirring bar, a dropping funnel, a thermometer and a collection receiver, 56.7 g of isobutanol and 85.3 g of 1,8-diazabicyclo [5.4.0]undec-7-ene (DBU) were placed; then the contents were placed in a nitrogen atmosphere, and then the reactor was heated to 60° C. When the internal temperature became constant, 50 g of the methanesulfonyl fluoride obtained in Production Example 1 was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 3 hours. Meanwhile, the distilled organic component was collected in a receiver immersed in a dry ice-ethanol bath. The organic substance collected in the receiver was analyzed with gas chromatography, and 23.0 g of isobutyl fluoride, the target product, was found to be obtained (yield with reference to methanesulfonyl fluoride: 59.3%).

The structure of the target product was identified on the basis of the $^1$H-NMR spectrum and the $^{19}$F-NMR spectrum.

$^1$H-NMR (CDCl$_3$, TMS) δ ppm: 1.03 (t, 3H×2), 1.97 (m, 1H), 4.41 (m, 2H), 4.45 (m, 2H)

$^{19}$F-NMR (CDCl$_3$, CFCl$_3$) δ ppm: −220 (m, F)

Example 8

In a 300 ml volume glass reactor equipped with a stirring bar, a dropping funnel, a thermometer and a collection receiver, 56.7 g of 1-butanol and 85.3 g of 1,8-diazabicyclo [5.4.0]undec-7-ene (DBU) were placed; then the contents were placed in a nitrogen atmosphere, and then the reactor was heated to 60° C. When the internal temperature became constant, 50 g of the methanesulfonyl fluoride obtained in Production Example 1 was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 2 hours. Meanwhile, the distilled organic component was collected in a receiver immersed in a dry ice-ethanol bath. The organic substance collected in the receiver was analyzed with gas chromatography, and 26.9 g of 1-fluorobutane, the target product, was found to be obtained (yield with reference to methanesulfonyl fluoride: 62.5%).

The structure of the target product was identified on the basis of the $^1$H-NMR spectrum and the $^{19}$F-NMR spectrum.

$^1$H-NMR (CDCl$_3$, TMS) δ ppm: 0.95 ppm (t, 3H), 1.43 (m, 2H), 1.70 (m, 2H), 4.45 (dt, 2H)

$^{19}$F-NMR (CDCl$_3$, CFCl$_3$) δ ppm: −219 ppm (m, F)

Comparative Example 1

In a 1-L volume glass reactor equipped with a stirrer, a dropping funnel and a collection trap, 86 g of spray dried potassium fluoride (manufactured by Aldrich Corp.) and 400 ml of diethylene glycol were placed; then nitrogen was introduced into the reactor from the outlet pipe of the collection trap, and thus the inside atmosphere of the reactor was a nitrogen atmosphere. The reactor was immersed in an oil bath and was heated to 90° C. 135 g of 2-(p-toluenesulfonyloxy)butane was added dropwise to the reactor from the dropping funnel over 2.5 hours. The reaction was continued at 90° C. for 8 hours, and the volatile component produced by the reaction was collected in the collection trap immersed in a dry ice-ethanol bath. Subsequently, the temperature of the oil bath was decreased to 80° C., and then two glass traps immersed in the dry ice-ethanol bath were connected in series to the reactor. Moreover, to the outlet of the glass traps, a pressure controller and a vacuum pump were connected. The vacuum pump was started, the pressure controller was used, and thus the internal pressure of the system was decreased in a stepwise manner to 50 to 45 kPa, subsequently to 35 to 30 kPa, and further to 30 to 25 kPa, and thus, the volatile component was recovered in the glass traps. The content of the first collection trap and the contents of the two glass traps were combined, and the resulting combined contents were analyzed with gas chromatography; consequently, only 13.5 g of 2-fluorobutane was obtained (yield with reference to 2-(p-toluenesulfonyloxy)butane: 29.1%).

Comparative Example 2

A reaction was performed in the same manner as in Example 1 except that the base was altered from 85.3 g of DBU in Example 1 to 64.6 g of 1,1,3,3-tetramethylguanidine (TMG). The organic substance collected in the receiver was analyzed with gas chromatography, and 6.8 g of 2-fluorobutane, the target product, was found to be obtained (yield with reference to methanesulfonyl fluoride: 17.5%).

Reference Example 1

In a 300 ml volume glass reactor equipped with a stirring bar a dropping funnel, a thermometer and a collection receiver, 57 parts of 2-butanol and 85.3 g of DBU were placed; then the contents were placed in a nitrogen atmosphere; subsequently, the reactor was placed in a room-temperature atmosphere, while the contents of the reactor were being stirred, 50 g of the methanesulfonyl fluoride produced in Production Example 1 was added dropwise to the reactor from the dropping funnel over approximately 1 hour. After the completion of the dropwise addition, the reaction was continued for further 19 hours. Meanwhile, the distilled organic component was collected in a receiver immersed in a dry ice-ethanol bath. After the completion of the reaction, to the outlet of the glass traps, a pressure controller and a vacuum pump were connected. The vacuum pump was started, the pressure controller was used, and thus the internal pressure of the system was decreased in a stepwise manner to 50 to 45 kPa, subsequently to 35 to 30 kPa, and further to 30 to 25 kPa, and thus, the volatile component was recovered in the glass traps. The content of the first collection receiver and the contents of the glass traps were combined, and the resulting combined contents were analyzed with gas chromatography; consequently, 11.4 g of 2-fluorobutane, the target product, was obtained (yield with reference to methanesulfonyl fluoride: 29.4%).

As can be seen in Examples 1 to 8, the target products were able to be obtained in a good yield.

On the other hand, as can be seen in the case based on a conventional method (Comparative Example 1), and in the case where as the base, the amidine base or the phosphazene base was not used (a guanidine base was used) (Comparative Example 2), the target products were not able to be obtained in a good yield.

In addition, as can be seen in the case performing the reaction at room temperature (Reference Example 1), as compared with the case performing the reaction at 60° C. or higher (Examples), the target product was not able to be obtained in a good yield.

Production Example 4

Synthesis of 1,8-diazabicyclo[5.4.0]undec-7-ene (DBU)-methanesulfonate Complex

In a 300 ml volume glass reactor equipped with a stirring bar, a dropping funnel, a thermometer and a collection receiver, 56.7 g of 2-butanol and 85.3 g of DBU were placed; then the contents were placed in a nitrogen atmosphere, and then the reactor was heated to 60° C. When the internal temperature became constant, 50 g of methanesulfonyl fluoride was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 27.6 g of 2-fluorobutane, the target product, was found to be obtained (yield with reference to methanesulfonyl fluoride: 71.2%).

In the glass reactor, DBU-methanesulfonate complex remained as a viscous oily dark brown substance.

Production Example 5

Synthesis of DBU-ethanesulfonate Complex

In a 300 ml volume glass reactor equipped with a stirring bar, a dropping funnel, a thermometer and a collection receiver, 56.7 g of 2-butanol and 85.3 g of DBU were placed; then the contents were placed in a nitrogen atmosphere, and then the reactor was heated to 60° C. When the temperature of the thermometer became constant, 57.2 g of ethanesulfonyl fluoride was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 27.5 g of 2-fluorobutane, the target product, was found to be obtained (yield with reference to ethanesulfonyl fluoride: 70.9%).

In the glass reactor, DBU-ethanesulfonate complex remained as a viscous oily dark brown substance.

Production Example 6

Synthesis of 1,5-diazabicyclo[4.3.0]non-5-ene (DBN)-methanesulfonate Complex

In a 300 ml volume glass reactor equipped with a stirring bar, a dropping funnel, a thermometer and a collection receiver, 56.7 g of 2-butanol and 69.7 g of DBN were placed; then the contents were placed in a nitrogen atmosphere, and then the reactor was heated to 60° C. When the internal temperature became constant, 50 g of methanesulfonyl fluoride was added dropwise to the reactor from the dropping funnel over approximately 1 hour. After the completion of the dropwise addition, the reaction was continued at 60° C. for further 5 hours, and then the reactor was increased in temperature to 100° C., and the reaction was continued for further 1 hour. Meanwhile, the distilled organic component was collected in a receiver immersed in a dry ice-ethanol bath. The organic substance collected in the receiver was analyzed with gas chromatography, and 19.4 g of 2-fluorobutane, the target product, was found to be obtained (yield with reference to methanesulfonyl fluoride: 50%)

In the glass reactor, DBN-methanesulfonate complex remained as a viscous oily dark brown substance.

Example 9

In a glass beaker equipped with a stirring bar, 147 g of the crude product of DBU-methanesulfonate complex recovered in Production Example 4 was placed, and was dissolved in 120 ml of toluene. While the resulting solution was being stirred, 72.5 g of a 48 wt % aqueous potassium hydroxide solution was added dropwise to the resulting solution at room temperature (25° C., hereinafter the same shall apply) over approximately 10 minutes. In the beaker, a large amount of solid content was precipitated while heat was being generated. After 20 minutes, 70 g of water was added to dissolve the solid content. Then, the content of the beaker was transferred into a separating funnel, and separated into two layers, namely, the toluene layer and the aqueous layer.

The aqueous layer, the lower layer, was extracted into a beaker, 120 ml of toluene was newly added in the beaker, and the resulting mixture was strongly stirred. The content of the beaker was again transferred into a separating funnel, and allowed to stand still; then the aqueous layer, the lower layer, was extracted into a beaker.

The previously obtained toluene layer, the upper layer, was combined with the toluene layer, the upper layer, and the combined toluene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 135° C., and thus the extraction of the toluene-water azeotropic mixture was performed. After approximately 2 hours, the distillation amount of water showed no variation, and accordingly heating was terminated and the reactor was cooled to room temperature. The toluene solution in the reactor was transferred into a glass flask, and the toluene was distilled off with a rotary evaporator. The residue in the flask was subjected to a simple distillation while the pressure was being reduced with a vacuum pump, and 72.0 g of the fraction at a column top temperature of 90° C. was recovered (recovery rate with reference to DBU used in Production Example 4: 84.4%).

Example 10

In a glass beaker equipped with a stirring bar, 147 g of the crude product of DBU-methanesulfonate complex recovered in Production Example 4 was placed, and was dissolved in 120 ml of xylene. While the resulting solution was being stirred, 72.5 g of a 48 wt % aqueous potassium hydroxide solution was added dropwise to the resulting solution at room temperature over approximately 10 minutes. In the beaker, a large amount of solid content was precipitated while heat was being generated.

After 20 minutes, 60 g of water was added to dissolve the solid content. The content of the beaker was transferred into a separating funnel, and separated into two layers, namely, the aqueous layer and the xylene layer. The aqueous layer, the lower layer, was extracted into a beaker, 120 ml of xylene was newly added in the beaker, and the resulting mixture was strongly stirred. The content of the beaker was again transferred into a separating funnel, and allowed to stand still; then the aqueous layer, the lower layer, was extracted into a beaker.

The previously obtained xylene layer was combined with the xylene layer, the upper layer, and the combined xylene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 150° C., and thus the extraction of the xylene-water azeotropic mixture was performed. After approximately 3.5 hours, the distillation amount of water showed no variation, and accordingly heating was terminated and the reactor was cooled to room temperature. The xylene solution in the reactor was transferred into a glass flask, and the xylene was distilled off with a rotary evaporator. The residue in the flask was subjected to a simple distillation while the pressure was being reduced with a vacuum pump, and 63.3 g of the fraction at a column top temperature of 90° C. was recovered (recovery rate with reference to DBU used in Production Example 4: 74.2%).

Example 11

In a glass beaker equipped with a stirring bar, 147 g of the crude product of DBU-methanesulfonate complex recovered in Production Example 4 was placed, and was dissolved in 120 ml of toluene. While the resulting solution was being stirred, 48 g of a 50 wt % aqueous sodium hydroxide solution was added dropwise to the resulting solution at room temperature over approximately 10 minutes. In the beaker, a large amount of solid content was precipitated while heat was being generated. After 20 minutes, 70 g of water was added to dissolve the solid content, and the resulting solution was allowed to stand still. The content of the beaker was transferred into a separating funnel, and separated into two layers, namely, the aqueous layer and the toluene layer. The aqueous layer, the lower layer, was extracted into a beaker, 120 ml of toluene was newly added in the beaker, and the resulting mixture was strongly stirred. The content of the beaker was again transferred into a separating funnel, and allowed to stand still; then the aqueous layer, the lower layer, was extracted into a beaker. The previously obtained toluene layer was combined with the toluene layer, the upper layer, and the combined toluene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 135° C., and thus the extraction of the toluene-water azeotropic mixture was performed. After approximately 3.5 hours, the distillation amount of water showed no variation, and accordingly heating was terminated and the reactor was cooled to room temperature. The toluene solution in the reactor was transferred into a glass flask, and the toluene was distilled off with a rotary evaporator. In the flask, 55.1 g of an oily substance remained (recovery rate with reference to DBU used in Production Example 4: 64.6%).

Example 12

In a glass beaker equipped with a stirring bar, 147 g of the crude product of DBU-methanesulfonate complex recovered in Production Example 4 was placed, and was dissolved in 120 ml of toluene. While the resulting solution was being stirred, an aqueous solution obtained by dissolving 87.5 g of cesium hydroxide hydrate in 40 g of water was added dropwise to the resulting solution at room temperature over approximately 15 minutes. In the beaker, a large amount of solid content was precipitated while heat was being generated. After approximately 30 minutes, 10 g of water was added to dissolve the solid content, and then the resulting solution was allowed to stand still. The content of the beaker was transferred into a separating funnel, and separated into two layers, namely, the aqueous layer and the toluene layer. The aqueous layer, the lower layer, was extracted into a beaker, 120 ml of toluene was newly added in the beaker, and the resulting mixture was strongly stirred. The content of the beaker was again transferred into a separating funnel, and allowed to stand still; then the aqueous layer, the lower layer, was extracted into a beaker. The previously obtained toluene layer was combined with the toluene layer, the upper layer, and the combined toluene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 135° C., and thus the extraction of the toluene-water azeotropic mixture was performed. After approximately 3 hours, the distillation amount of water showed no variation, and accordingly heating was terminated and the reactor was cooled to room temperature. The toluene solution in the reactor was transferred into a glass flask, and the toluene was distilled off with a rotary evaporator. The residue in the flask was subjected to a simple distillation while the pressure was being reduced with a vacuum pump, and 54.8 g of the fraction at a column top temperature of 90° C. was recovered (recovery rate with reference to DBU used in Production Example 4: 64.2%).

Example 13

In a glass beaker equipped with a stirring bar, 153 g of the crude product of DBU-ethanesulfonate complex recovered in Production Example 5 was placed, and was dissolved in 120 ml of toluene. While the resulting solution was being stirred, 67.8 g of a 48 wt % aqueous potassium hydroxide solution was added dropwise to the resulting solution at room temperature over approximately 10 minutes. In the beaker, a large amount of solid content was precipitated while heat was being generated. After 20 minutes, 60 g of water was added to dissolve the solid content, and the resulting solution was allowed to stand still. The content of the beaker was transferred into a separating funnel, and separated into two layers, namely, the aqueous layer and the toluene layer. The aqueous layer, the lower layer, was extracted into a beaker, 120 ml of toluene was newly added in the beaker, and the resulting mixture was strongly stirred. The content of the beaker was again transferred into a separating funnel, and allowed to stand still; then the aqueous layer, the lower layer, was extracted into a beaker. The previously obtained toluene layer was combined with the toluene layer, the upper layer, and the combined toluene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 135° C., and thus the extraction of the toluene-water azeotropic mixture was performed. After approximately 3 hours, the distillation amount of water showed no variation, and accordingly heating was terminated and the reactor was cooled to room temperature. The toluene solution in the reactor was transferred into a glass flask, and the toluene was distilled off with a rotary evaporator. The residue in the flask was subjected to a simple distillation while the pressure was being reduced with a vacuum pump, and 66.9 g of the fraction at a column top temperature of 90° C. was recovered (recovery rate with reference to DBU used in Production Example 5: 78.7%).

Example 14

A reaction was performed in the same manner as in Production Example 4 except that the DBU used in the Production Example 4 was altered to the DBU obtained in Example 7. The organic substance collected in the receiver was analyzed with gas chromatography, and 27 parts of 2-fluorobutane, the target product, was found to be obtained (yield with reference to methanesulfonyl fluoride: 71%) As can be seen from this result, by using the DBU recovered by the present invention, it is possible to obtain the reaction achievement equivalent to the reaction achievement of the case using fresh DBU.

Example 15

In a glass beaker equipped with a stirring bar, 145 g of the crude product of DBN-methanesulfonate complex recovered in Production Example 6 was placed, and was dissolved in 120 ml of toluene. While the resulting solution was being stirred, 67.8 g of a 48 wt % aqueous potassium hydroxide solution was added dropwise to the resulting solution at room temperature over approximately 10 minutes. In the beaker, a large amount of solid content was precipitated while heat was being generated. After 20 minutes, 40 g of water was added to dissolve the solid content, and the resulting solution was allowed to stand still. The content of the beaker was transferred into a separating funnel, and separated into two layers, namely, the aqueous layer and the toluene layer. The aqueous layer, the lower layer, was extracted into a beaker, 120 ml of toluene was newly added in the beaker, and the resulting mixture was strongly stirred. The content of the beaker was again transferred into a separating funnel, and allowed to stand still; then the aqueous layer, the lower layer, was extracted into a beaker. The previously obtained toluene layer was combined with the toluene layer, the upper layer, and the combined toluene layers were placed in a glass reactor equipped with a stirring bar. In the glass reactor, a Dean-Stark water separator was arranged, a Dimroth condenser was arranged in the upper portion, and a cooling medium at 0° C. was circulated. The glass reactor was heated to 135° C., and thus the extraction of the toluene-water azeotropic mixture was performed. After approximately 2.5 hours, the distillation amount of water showed no variation, and accordingly heating was terminated and the reactor was cooled to room temperature. The toluene solution in the reactor was transferred into a glass flask, and the toluene was distilled off with a rotary evaporator. The amount of the residue in the flask was 43.9 g (recovery rate with reference to the DBU used in the Production Example 6: 64.7%).

Comparative Example 3

The same operations as in Example 9 were performed except that toluene in Example 9 was altered to methylcyclohexane and no separation of water based on azeotropic distillation was performed. DBU was recovered in an amount of only 5.4 g (recovery rate with reference to DBU used in Production Example 4: 6%).

The invention claimed is:

1. A method for producing a fluorinated alkane represented by the formula (2): $R^2$—F ($R^2$ represents an alkyl group having 3 to 5 carbon atoms), wherein an alcohol having 3 to 5 carbon atoms is fluorinated by a fluorinating agent represented by the formula (1): $R^1SO_2F$ ($R^1$ represents a methyl group, an ethyl group or an aromatic group) in the absence of a solvent, and in the presence of an amidine base, and wherein the base is the amidine base represented by the following formula (4):

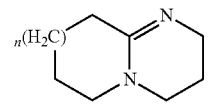

(4)

(in the formula, n is 0 or 2).

2. The method for producing a fluorinated alkane according to claim 1, wherein the reaction is performed by adding the fluorinating agent to the mixture of the alcohol having 3 to 5 carbon atoms and the base at 60° C. to 150° C.

3. The method for producing a fluorinated alkane according to claim 1, wherein the fluorinating agent is methanesulfonyl fluoride.

4. The method for producing a fluorinated alkane according to claim 1, wherein the fluorinated alkane is 2-fluorobutane.

5. A method for producing a fluorinated alkane represented by the formula (2): $R^2$—F ($R^2$ represents an alkyl group having 3 to 5 carbon atoms), wherein an alcohol having 3 to 5 carbon atoms is fluorinated by a fluorinating agent represented by the formula (1): $R^1SO_2F$ ($R^1$ represents a methyl group, an ethyl group or an aromatic group) in the absence of a solvent, and in the presence of an amidine base, and wherein the base is 1,8-diazabicyclo[5.4.0]undec-7-ene.

6. The method for producing a fluorinated alkane according to claim 5, wherein the reaction is performed by adding the fluorinating agent to the mixture of the alcohol having 3 to 5 carbon atoms and the base at 60° C. to 150° C.

7. The method for producing a fluorinated alkane according to claim 5, wherein the fluorinating agent is methanesulfonyl fluoride.

8. The method for producing a fluorinated alkane according to claim 5, wherein the fluorinated alkane is 2-fluorobutane.

* * * * *